(12) United States Patent
Xu et al.

(10) Patent No.: US 7,982,080 B2
(45) Date of Patent: Jul. 19, 2011

(54) PRODUCTION OF AROMATICS FROM ALIPHATICS

(76) Inventors: Teng Xu, Hampton, NJ (US); Kenneth R. Clem, Humble, TX (US); Jeremy J. Patt, Lake Jackson, TX (US); J. Scott Buchanan, Lambertville, NJ (US); Larry L. Iaccino, Seabrook, TX (US)

(*) Notice: Subject to any disclaimer, the term of this patent is extended or adjusted under 35 U.S.C. 154(b) by 502 days.

(21) Appl. No.: 12/166,153

(22) Filed: Jul. 1, 2008

(65) Prior Publication Data

US 2009/0030253 A1    Jan. 29, 2009

Related U.S. Application Data

(60) Provisional application No. 60/951,605, filed on Jul. 24, 2007.

(51) Int. Cl.
  *C07C 2/46* (2006.01)
(52) U.S. Cl. .................................... 585/418; 585/419
(58) Field of Classification Search .............. 585/418, 585/419
  See application file for complete search history.

(56) References Cited

U.S. PATENT DOCUMENTS

| | | | |
|---|---|---|---|
| 4,720,602 | A | 1/1988 | Chu |
| 4,727,206 | A | 2/1988 | Clayson et al. |
| 4,891,463 | A | 1/1990 | Chu |
| 5,026,937 | A | 6/1991 | Bricker |
| 5,336,825 | A | 8/1994 | Choudhary et al. |
| 6,239,057 | B1 | 5/2001 | Ichikawa et al. |
| 6,426,442 | B1 | 7/2002 | Ichikawa et al. |

FOREIGN PATENT DOCUMENTS

| WO | WO03/000826 | 1/2003 |
|---|---|---|
| WO | 2006/068814 | 6/2006 |

OTHER PUBLICATIONS

Liu et al., "Bifunctional Catalysis of Mo/HZSM-5 in the Dehydroaromatization of Methane to Benzene and Naphthalene XAFS/TG/DTA/MASS/FTIR Characterization and Supporting Effects", Journal of Catalysis, 181, (1999), pp. 175-188.
Liu et al., "Methane Dehydrogenation and Aromatization over Mo/HZSM-5: In Situ FT-IR Characterization of its Acidity and the Interaction between Mo Species and HZSM-5", Journal of Catalysis, 185, (1999), pp. 386-392.
Borry et al., "Structure and Density of Mo and Acid Sites in Mo-Exchanged H-ZSM5 Catalysts for Nonoxidative Methane Conversion", J. Phys. Chem. B., 103, (1999), pp. 5787-5796.
Tessonnier et al., "Quantitative Measurement of the Bronsted Acid Sites in Solid Acids: Toward a Single-Site Design of Mo-Modified ZSM-5 Zeolite", J. Phys. Chem. B 2006, 110, pp. 10390-10395.
Tessonnier et al., "Methane dehydro-aromatization on Mo/ZSM-5: About the hidden role of Bronsted acid sites", Applied Catalysis A: General (2007), APCATA—11153, No. of pages: 10.
Liu B. et al., "*Non-oxidative dehydroaromatization of methane over Ga-promoted Mo/HZSM-5-based catalysts*" Applied Catalysis A: General, 2001, vol. 214, No. 1, pp. 95-102.

*Primary Examiner* — Thuan Dinh Dang
(74) *Attorney, Agent, or Firm* — Andrew B. Griffis

(57) ABSTRACT

In a process for converting a low carbon number aliphatic hydrocarbon to higher hydrocarbons including aromatic hydrocarbons, a feed containing the aliphatic hydrocarbon is contacted with a dehydrocyclization catalyst under conditions effective to convert the aliphatic hydrocarbon to aromatic hydrocarbons and produce an effluent stream comprising aromatic hydrocarbons and hydrogen. The dehydrocyclization catalyst comprises a metal or metal compound and a molecular sieve wherein the ratio of the amount of any Bronsted acid sites in the catalyst to the amount of said metal in the catalyst is less than 0.4 mol/mol of said metal.

9 Claims, 5 Drawing Sheets

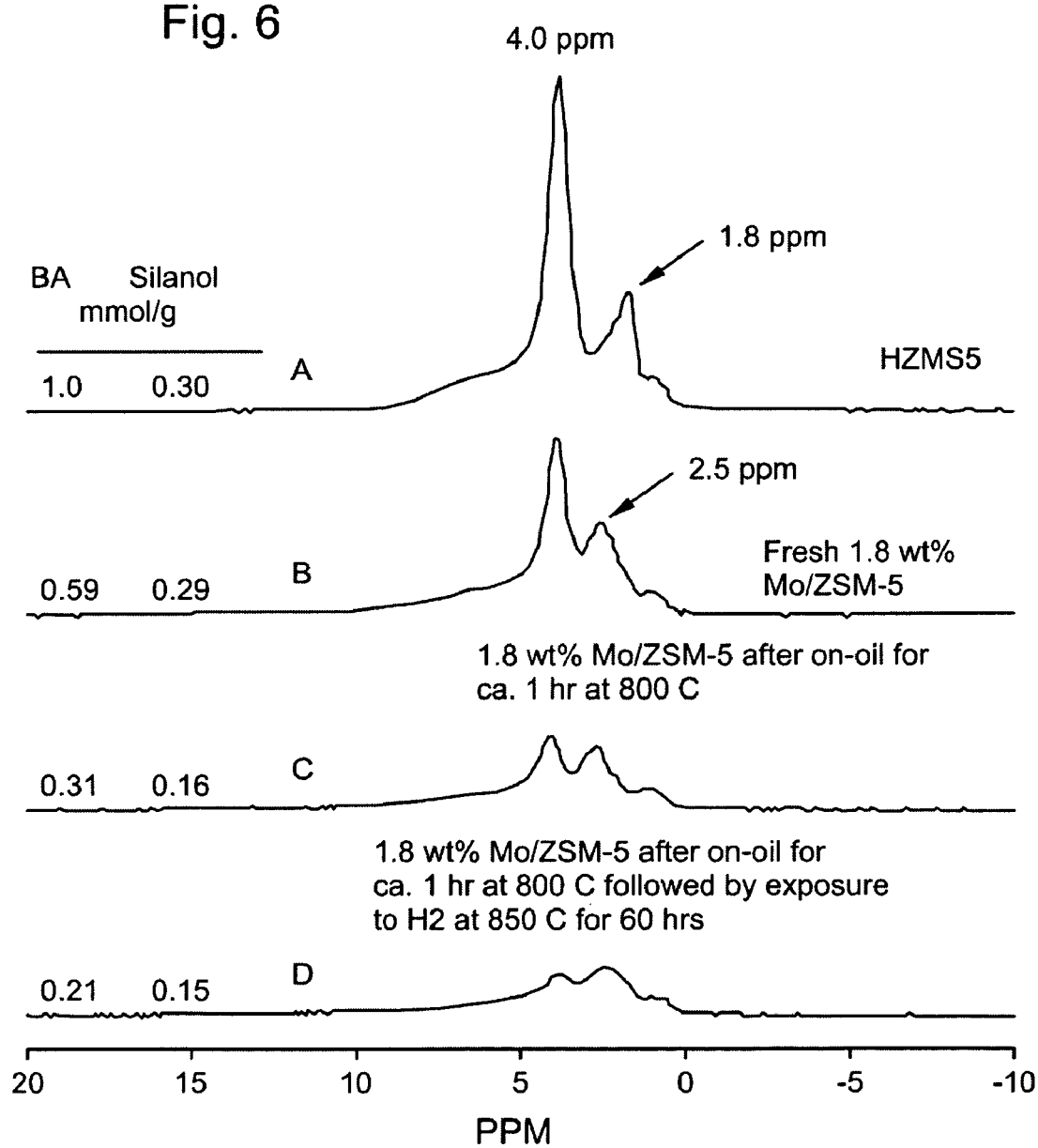

PRODUCTION OF AROMATICS FROM ALIPHATICS

PRIORITY CLAIM

This application claims the benefit of U.S. Provisional Application No. 60/951,605, filed Jul. 24, 2007, the entirety of which is incorporated by reference.

FIELD

This invention relates to a process for producing aromatic hydrocarbons from low carbon number (containing 1 to 5 carbon atoms) aliphatic hydrocarbons, especially methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane and other low carbon number (containing 1 to 5 carbon atoms) aliphatic hydrocarbons to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydroaromatization or reductive coupling. This process typically involves contacting the methane with a catalyst comprising a metal, such as rhenium, tungsten or molybdenum, supported on a zeolite, such as ZSM-5, at high temperature, such as 600° C. to 1000° C. Frequently, the catalytically active species of the metal is the zero valent elemental form or a carbide or oxycarbide.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole % hydrogen and 50 mole % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPaa) and a gas hourly space velocity of 400 to 7,500 $hr^{-1}$.

Moreover, U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is said to increase the yield of benzene and the stability of the catalyst.

Further in our International Patent Publication No. WO 2006/068814, published Jun. 29, 2006, we have described a process for converting methane to higher hydrocarbons including aromatic hydrocarbons, the process comprising contacting a feed containing methane with a dehydrocyclization catalyst, conveniently molybdenum, tungsten and/or rhenium or a compound thereof on ZSM-5 or an aluminum oxide, under conditions effective to convert said methane to aromatic hydrocarbons and produce a first effluent stream comprising aromatic hydrocarbons and hydrogen, wherein said first effluent stream comprises at least 5 wt % more aromatic rings than said feed; and reacting at least part of the hydrogen from said first effluent stream with an oxygen-containing species to produce a second effluent stream having a reduced hydrogen content compared with said first effluent stream.

However, the successful application of reductive coupling to produce aromatics on a commercial scale requires the solution of a number of serious technical challenges. For example, the reductive coupling process is both endothermic and thermodynamically limited. Thus the cooling effect caused by the reaction lowers the reaction temperature sufficiently to greatly reduce the reaction rate and total thermodynamic conversion if significant make-up heat is not provided to the process.

In addition, the process tends to produce carbon and other non-volatile materials, collectively referred to as "coke", that accumulate on the catalyst resulting in reduced activity and potentially undesirable selectivity shifts, as well as loss of valuable feedstock. Although the coke can be removed from the catalyst by oxidative or reductive regeneration, this leads to lost production time as well as potential damage to the catalyst. There is therefore interest in developing dehydrocyclization catalysts that exhibit reduced coke selectivity without loss in selectivity to the desired aromatic products.

According to the invention, it has now been found that the metal-containing zeolite catalysts normally employed in the conversion of methane to aromatic hydrocarbons generally contain Bronsted acid sites. In the past, these Bronsted acid sites were considered desirable and in fact the scientific literature teaches that these sites are essential to the good performance of the catalyst in methane aromatization [see, for example, Liu et al., *Journal of Catalysis*, 185, 386-393 (1999), Liu et al., *Journal of Catalysis*, 181, 175-188 (1999) and Borry et al., *J. Phys. Chem.*, 103, 5787-5796 (1999)]. Surprisingly, however, it has now been found that these Bronsted acid sites are not necessary for the production of aromatics from low carbon number aliphatic hydrocarbons and in fact are highly coke selective thereby resulting in increased coke production during methane conversion. In contrast, reducing the concentration of these acid sites has been found to decrease the coke selectivity of the catalyst.

SUMMARY

In one aspect, the present invention resides in a process for converting a low carbon number aliphatic hydrocarbon to higher hydrocarbons including aromatic hydrocarbons, the process comprising contacting a feed containing said aliphatic hydrocarbon with a dehydrocyclization catalyst under conditions effective to convert said aliphatic hydrocarbon to aromatic hydrocarbons and produce an effluent stream comprising aromatic hydrocarbons and hydrogen, wherein said dehydrocyclization catalyst comprises a metal or metal compound and a molecular sieve and wherein the ratio of the amount of any Bronsted acid sites in the catalyst to the amount of said metal in the catalyst is less than 0.4 mol/mol, such as less than 0.1 mol/mol, for example less than 0.01 mol/mol, of said metal.

In a further aspect, the present invention resides in a process for converting a low carbon number aliphatic hydrocarbon to higher hydrocarbons including aromatic hydrocarbons, the process comprising contacting a feed containing said aliphatic hydrocarbon with a dehydrocyclization catalyst under conditions effective to convert said aliphatic hydrocarbon to aromatic hydrocarbons and produce an effluent stream comprising aromatic hydrocarbons and hydrogen, wherein said dehydrocyclization catalyst comprises a metal or metal compound and an aluminosilicate molecular sieve and wherein the amount of any Bronsted acid sites in the catalyst is less than 0.1 mol, for example less than 0.01 mol, per mol of the framework Al in the molecular sieve.

In yet a further aspect, the present invention resides in a process for converting a low carbon number aliphatic hydrocarbon to higher hydrocarbons including aromatic hydrocarbons, the process comprising contacting a feed containing said aliphatic hydrocarbon with a dehydrocyclization catalyst under conditions effective to convert said aliphatic hydrocarbon to aromatic hydrocarbons and produce an effluent stream comprising aromatic hydrocarbons and hydrogen, wherein said dehydrocyclization catalyst comprises a metal or metal compound and an aluminosilicate molecular sieve having a silica to alumina molar ratio less than 100, and wherein the amount of any Bronsted acid sites in the catalyst is less than 0.1 mmol, for example less than 0.01 mmol, per gram of the molecular sieve.

In still yet a further aspect, the present invention resides in a process for converting a low carbon number aliphatic hydrocarbon to higher hydrocarbons including aromatic hydrocarbons, the process comprising contacting a feed containing said aliphatic hydrocarbon with a dehydrocyclization catalyst under conditions effective to convert said aliphatic hydrocarbon to aromatic hydrocarbons and produce an effluent stream comprising aromatic hydrocarbons and hydrogen, wherein said dehydrocyclization catalyst comprises a metal or metal compound and a molecular sieve having Bronsted acid sites and wherein said catalyst has been pretreated to reduce the number of said Bronsted acid sites on the molecular sieve.

Conveniently, said pretreatment of said catalyst reduces the number of Bronsted acid sites by at least 20%, such as at least 50%, for example at least 75% as compared with the untreated catalyst.

In one embodiment, pretreatment of said catalyst to reduce the number of Bronsted acid sites comprises heating the catalyst in the presence of a gas comprising hydrogen, such as a gas comprising a mixture of hydrogen and a low carbon number aliphatic hydrocarbon, such as methane. Conveniently, said heating in the presence of hydrogen is conducted at a temperature of about 600° C. to about 1000° C. for a time of about 0.1 hours to about 100 hours.

In another embodiment, pretreatment of said catalyst to reduce the number of Bronsted acid sites comprises ion exchange to replace hydrogen ions with metal ions.

Conveniently, said molecular sieve comprises ZSM-5 and said metal comprises molybdenum, rhenium and/or tungsten.

In another aspect, the present invention resides in a process for converting a low carbon number aliphatic hydrocarbon to higher hydrocarbons including aromatic hydrocarbons, the process comprising:
(a) contacting a feed containing said aliphatic hydrocarbon with an inventory of a dehydrocyclization catalyst in a reaction zone under conditions effective to convert said aliphatic hydrocarbon to aromatic hydrocarbons and generate coke on the catalyst, said dehydrocyclization catalyst comprising a metal or metal compound and a molecular sieve;
(b) periodically contacting at least a portion of said catalyst from said inventory with a regeneration gas under conditions effective to at least partially remove coke from said catalyst portion;
(c) adding fresh dehydrocyclization catalyst to make up for losses from said inventory during (a) and (b), wherein said addition is controlled such that the ratio of the amount of any Bronsted acid sites in the catalyst inventory to the amount of said metal in the catalyst inventory is less than 0.1 mol/mol of said metal.

BRIEF DESCRIPTION OF THE DRAWINGS

FIGS. (2)*a* and (*b*) are graphs plotting time against temperature and catalyst % weight change in thermogravimetric studies of the coking of the HZSM-5 of Example 1 without initial hydrogen treatment [FIG. 2(*a*)] and after initial hydrogen treatment at 850° C.

FIGS. 6 (a) to (d) show the $^1$H NMR spectra of the HZSM-5 used in Example 4 [FIG. 6(a)], of the fresh 1.8 wt % Mo/ZSM-5 of Example 4 [FIG. 6(b)], of the 1.8 wt % Mo/ZSM-5 of Example 4 after exposure to methane/hydrogen at 800° C. for 1 hr then methane at 800° C. for 1 hr [FIG. 6(c)] and of the 1.8 wt % Mo/ZSM-5 of Example 4 after exposure to methane/hydrogen at 800° C. for 1 hr then methane at 800° C. for 1 hr followed by exposure to $H_2$ at 850° C. for 60 hrs [FIG. 6(d)].

DETAILED DESCRIPTION OF THE EMBODIMENTS

Figure 1:
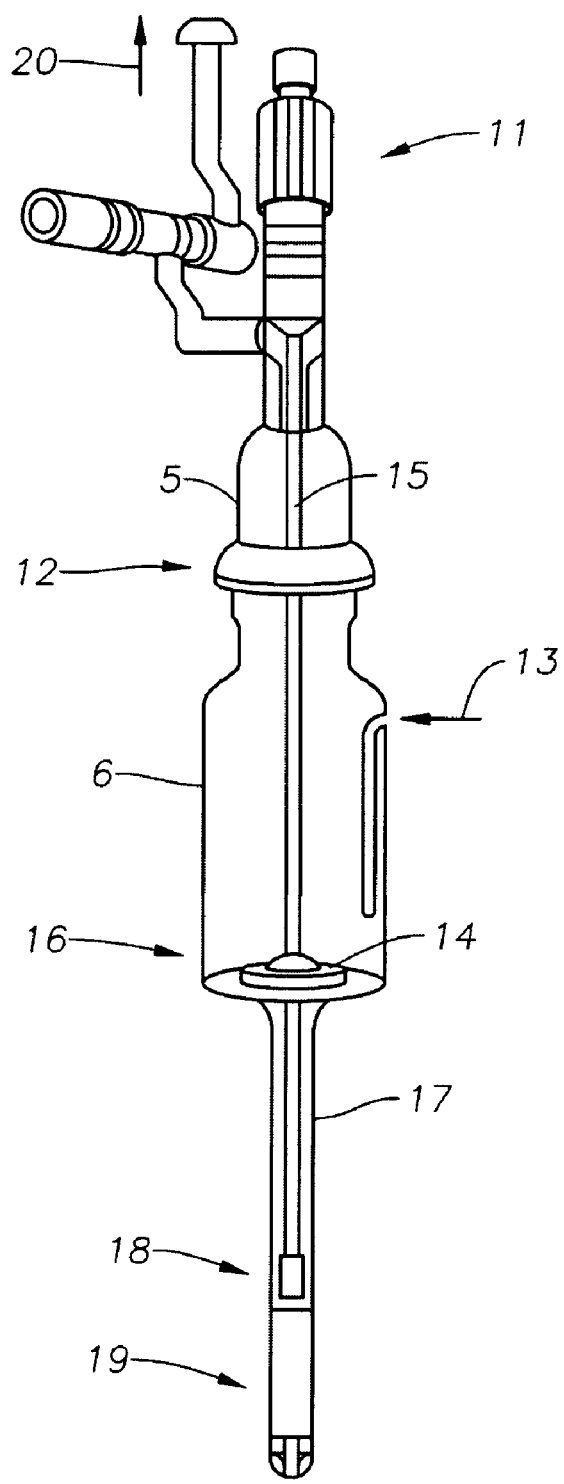
FIG. 1 is a diagram of a device for measuring the proton density of catalyst samples by NMR.

As used herein the term "low carbon number aliphatic hydrocarbon" means a saturated or unsaturated aliphatic hydrocarbon containing 1 to 5 carbon atoms, such as such as ethane, ethylene, acetylene, propane, propylene, n-butane, isobutane, butene, isobutene, propane, iso-propane, propenes, etc.

As used herein the term "higher hydrocarbon(s)" means hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) comprising at least one carbon atom and at least one non-hydrogen atom, e.g., methanol, ethanol, methylamine, and/or ethylamine.

As used herein the term "aromatic hydrocarbon(s)" means molecules containing one or more aromatic rings. Examples of aromatic hydrocarbons are benzene, toluene, xylenes, naphthalene, and methylnaphthalenes.

The terms "coke" and "carbonaceous material" are used herein interchangeably to mean carbon containing materials, which are essentially non-volatile solids at the reaction conditions, with a low hydrogen content relative to carbon content (such as a H/C molar ration of less than 0.8; most probably less than 0.5). These may include crystalline graphite, graphitic sheets, graphitic fragments, amorphous carbon, or other carbon containing structures which are essentially non-volatile solids at the reaction conditions.

The present invention provides a process for producing aromatic hydrocarbons by contacting a feedstock containing a low carbon number aliphatic hydrocarbon, typically together with $H_2$, $H_2O$, $O_2$, CO and/or $CO_2$, with a dehydrocyclization catalyst in a reaction zone under conditions effective to convert the aliphatic hydrocarbon to aromatic hydrocarbons and hydrogen. The dehydrocyclization catalyst comprises a metal or metal compound, typically molybdenum, and a molecular sieve, normally an aluminosilicate molecular sieve, wherein the ratio of the amount of any Bronsted acid sites in the catalyst to the amount of the metal in the catalyst is less than 0.1 mol of Bronsted acid sites per mol of said metal and typically is less than 0.1 mol of Bronsted acid sites per mol of the framework Al in the molecular sieve. As will be discussed in more detail below, measurements of Bronsted acid site density of a catalyst are conveniently achieved by NMR.

By maintaining the Bronsted acid site density at such low levels, it is found that the coke selectivity of the catalyst can be reduced without impairing the yield of aromatic hydrocarbons obtained when the catalyst is used in the aromatization of methane. Nevertheless, during the aromatization reaction, coke tends to build up on the catalyst and hence, in a continuous process, at least a portion of the catalyst inventory is periodically regenerated. In such a process, part of the catalyst inventory is inevitably lost as the reaction proceeds and so fresh catalyst is supplied the system to maintain the inventory at desired levels. In one embodiment of the present process, the addition of fresh catalyst is controlled such that the ratio of the amount of any Bronsted acid sites in the catalyst inventory to the amount of said metal in the catalyst inventory is less than 0.4 mol/mol, such as less than 0.1 mol/mol, of said metal.

Feedstock

Any feedstock containing one or more low carbon number aliphatic hydrocarbons can be used in the present process, although in general the feedstock will contain at least some methane. One particularly suitable methane-containing feedstock process is natural gas. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or ethane in a hydrogen rejection step.

Nitrogen and/or sulfur impurities are also typically present in methane-containing streams may be removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition to methane or other lower aliphatic hydrocarbon, the feed to the dehydrocyclization step may contain at least one of hydrogen, water, oxygen, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also a mixture of methane with higher hydrocarbons than methane, including aromatic hydrocarbons. Such higher hydrocarbons can be recycled from the hydrogen rejection step, added as separate co-feeds or can be present in the methane stream, such as, for example, when ethane is present in a natural gas feed. Higher hydrocarbons recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3+$ hydrocarbons.

Dehydrocyclization

In the dehydrocyclization step of the present process, the methane containing feedstock is contacted with a dehydrocyclization catalyst under conditions, normally non-oxidizing conditions and typically reducing conditions, effective to convert the methane to higher hydrocarbons, including benzene and naphthalene. The principal net reactions involved are as follows:

$$2CH_4 \leftrightarrow C_2H_4+2H_2 \quad \text{(Reaction 1)}$$

$$6CH_4 \leftrightarrow C_6H_6+9H_2 \quad \text{(Reaction 2)}$$

$$10CH_4 \leftrightarrow C_{10}H_8+16H_2 \quad \text{(Reaction 3)}$$

Carbon monoxide and/or dioxide that may be present in the feed improves catalyst activity and stability by facilitating reactions such as:

$$CO_2+\text{coke} \rightarrow 2CO \quad \text{(Reaction 4)}$$

but negatively impacts equilibrium by allowing competing net reactions, such as;

$$CO_2+CH_4 \leftrightarrow CO+2H_2 \quad \text{(Reaction 5).}$$

The catalyst used in the dehydrocyclization step comprises a hydrogenation/dehydrogenation metal or compound thereof dispersed on a molecular sieve support, particularly an aluminosilicate molecular sieve. Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Preferred metals are transition metals from Groups 6 to 10 of the Periodic Table of Elements [see Chemical and Engineering News, 63(5), 27 (1985)], especially molybdenum rhenium and/or tungsten.

Conveniently, the metal component is present in the dehydrocyclization catalyst in an amount between about 0.1% and about 20%, such as between about 1% and about 10%, by weight of the total catalyst. Generally, the metal will be present in the catalyst in elemental form or as a carbide species.

The molecular sieve employed in the dehydrocyclization catalyst may be a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

In addition to the hydrogenation/dehydrogenation metal and the molecular sieve support, the dehydrocyclization catalyst may include a binder to improve its physical and/or chemical properties. Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Examples of preferred catalysts include molybdenum, tungsten, rhenium and compounds and combinations thereof, especially molybdenum, on an aluminosilicate molecular sieve, particularly ZSM-5, having an as-synthesized silica to alumina molar ratio less than 100.

The metal component can be dispersed on the molecular sieve support by any means well known in the art such as co-precipitation, incipient wetness, evaporation, impregnation, spray-drying, sol-gel, ion-exchange, chemical vapor deposition, diffusion and physical mixing. In general, dispersion of the metal on the support involves reaction of the metal with Bronsted acid sites present on the molecular sieve so that, for example, for each mole of molybdenum dispersed on a zeolite support, generally one mole of acid site is consumed. However, after dispersion of the metal component on the molecular sieve support, there are usually residual acid sites on the catalyst since the amount of acid sites on support is typically greater than the amount of metal loaded. It has now been found that these residual acid sites are highly coke selective and hence result in increased coke production during methane conversion. It is therefore desirable to reduce or remove the excess Bronsted acid sites prior to methane conversion. In particular, it is desirable to ensure that the ratio of the amount of any Bronsted acid sites remaining in the catalyst to the amount of metal in the catalyst is less than 0.4 mol, such as less than 0.1 mol, for example less than 0.01 mol, of Bronsted acid sites per mol of said metal. Where the support is an aluminosilicate molecular sieve, it is desirable to ensure that the amount of any Bronsted acid sites in the catalyst is less than 0.1 mol, such as less than 0.01 mol, of Bronsted acid sites per mol of the framework Al in the molecular sieve and in general that the amount of any Bronsted acid sites in the catalyst is less than 0.1 mmol, such as less than 0.01 mmol, per gram of the molecular sieve.

Reduction of the amount of Bronsted acid sites in the metal-containing dehydrocyclization catalyst can be achieved in a number of ways. For example, the catalyst can be heated in the presence of gas comprising hydrogen, such as a mixture of hydrogen and at least one low carbon number aliphatic hydrocarbon, such as methane, at a temperature of about 600° C. to about 1000° C. for a time of at least 0.1 hours, such as about 0.1 hours to about 100 hours. Alternatively, it is possible to use additional metal cations to titrate Bronsted acid sites via a variety of methods, e.g., solids cation exchange. In any event, the treatment of the catalyst is normally conducted so as reduce the number of Bronsted acid sites on the catalysts by at least 20%, such as at least 50%, even as much as 75%, as compared with the untreated catalyst.

In addition to treatment to reduce Bronsted acid sites, the molecular sieve support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

In some embodiments, a non-catalytic particulate material may be supplied to the dehydrocyclization reaction in addition to the catalytic particulate material. The non-catalytic particulate material may be used as a material to transport energy (heat) into the system and/or to fill space as required providing the required hydrodynamic environment. The non-catalytic particulate material may form particulates without a binder or may be bound with an inorganic binder such as clay, silica, alumina, zirconia, or other metal oxide used to help maintain the physical integrity of the particles. Preferably the particles are of a substantially spherical shape. Examples of suitable non-catalytic particulate material are low surface area silica, alumina, ceramics, and silicon carbide.

The dehydrocyclization step is conducted by contacting the methane-containing feedstock with the dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the or each reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the dehydrocyclization reaction is conducted in a plurality of series-connected fluidized bed reactors in which particulate catalyst is cascaded in one direction from one reactor to the next adjacent reactor in the series, while the feed is passed through and between the reactors in the opposite direction.

The dehydrocyclization reaction is endothermic and hence the temperature in each dehydrocyclization reaction zone will tend to decrease from a maximum temperature to a minimum temperature as the reaction proceeds. Suitable conditions for the dehydrocyclization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydrocyclization reaction to reduce the temperature drop during the reaction and hence in some configurations it is possible to reduce the difference between the maximum and minimum temperatures to essentially zero. Alternatively, by supplying heated catalyst to the dehydrocyclization reaction, it is possible to produce an inverse temperature profile; that is with the process gas outlet reaction temperature being greater than the process gas inlet reaction temperature.

In one embodiment, the countercurrent flow of the feedstock and the particulate dehydrocyclization catalyst is arranged to produce an inverse temperature profile across dehydrocyclization reaction system, such that, despite the endothermic nature of the dehydrocyclization reaction, the difference between the reaction temperature of the gaseous effluent at the outlet from the dehydrocyclization reaction system and the reaction temperature of the methane-containing feed at the inlet to the dehydrocyclization reaction system is at least +10° C., such as at least +50° C., for example at least +100° C., and even at least +150° C.

In any event, since the dehydrocyclization reaction is endothermic, the catalytic particulate material enters the dehydrocyclization reaction system at a first, high temperature, typically about 800° C. to about 1200° C., such as about 900° C. to about 1100° C., and exits the reaction system at a second lower temperature, typically about 500° C. to about 800° C., such as about 600° C. to about 700° C. The total temperature difference of the catalytic particulate material across the reaction zones is at least 100° C.

Other conditions used in the dehydrocyclization reaction generally include a pressure of about 1 kPa to about 1000 kPa, such as about 10 to about 500 kPa, for example about 50 kPa to about 200 kPa and a weight hourly space velocity of about 0.01 to about 1000 $hr^{-1}$, such as about 0.1 to about 500 $hr^{-1}$, for example about 1 to about 20 $hr^1$. Conveniently, the dehydrocyclization step is conducted in the absence of $O_2$.

The major components of the effluent from the dehydrocyclization step are hydrogen, benzene, naphthalene, carbon monoxide, ethylene, and unreacted methane. Typically, the effluent contains at least 5 wt. %, such as at least 10 wt. %, for example at least 20 wt. %, conveniently at least 30 wt. %, more aromatic rings than the feed.

The benzene and naphthalene are separated from the dehydrocyclization effluent, for example, by solvent extraction followed by fractionation, and can be recovered as a product stream. However, as will be discussed below, at least part of these aromatic components can be submitted to an alkylation step, before or after product recovery, to produce higher value materials, such as xylenes. Moreover, as will be discussed below, the present process utilizes the hydrogen generated as a by-product of the dehydrocyclization reaction and in particular converts at least part of the hydrogen to higher value products.

Catalyst Regeneration

The dehydrocyclization reaction tends to deposit coke on the catalyst and hence, to maintain the activity of the dehydrocyclization catalyst, at least part of the catalyst must be continuously or intermittently regenerated. This is typically achieved by withdrawing a portion of the catalyst from the or each reaction zone, either on an intermittent, or a continuous basis, and is transferred to a separate regeneration zone. In the regeneration zone, the coked dehydrocyclization catalyst is contacted with a hydrogen-containing gas under conditions effective to convert at least a portion of the carbonaceous material thereon to methane. Generally, the hydrogen-containing gas does not contain significant quantities of methane or other hydrocarbons; typically with the hydrocarbon content being less than 20 mol %, such as less than 10 mol %, for example less than 2 mol %. In one embodiment, the hydrogen required for the regeneration is obtained at least in part from the hydrogen-containing effluent from the dehydrocyclization reaction.

Conveniently, the regeneration conditions comprise a temperature from about 700° C. to about 1200° C., such as from about 800° C. to about 1000° C., such as about 850° C. to about 950° C. and a pressure of at least 100 kPaa, such between about 150 kPaa and about 5000 kPaa. Generally, however, the coked dehydrocyclization catalyst removed from the or each reaction zone will be at a lower temperature than the optimum for regeneration and hence the removed catalyst is initially heating to a desired regeneration temperature by direct and/or indirect contact with combustion gases produced by combustion of a supplemental fuel. The heating is conducted in a heating zone which may be in the same vessel as the regeneration zone or which may be in a separate vessel from the regeneration zone.

By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, in the case of direct heat transfer to the dehydrocyclization catalyst, the use of an oxygen-lean atmosphere inhibits oxidation of metal carbides present in the catalyst and minimizes the average steam partial pressure thereby reducing catalyst hydrothermal aging.

Alternatively, a suitable supplemental fuel source is hydrogen and, in particular, part of the hydrogen generated as a by-product of the aromatization reaction.

The or each regeneration zone may be a reactor operated as a fluidized bed, an ebulating bed, a settling bed, a riser reactor or a combination thereof. In practice, each regeneration zone may include a plurality of reactors, such as a plurality of riser reactors connected in parallel or a plurality of reactors connected in series such as a riser reactor followed by a settling bed. After regeneration the catalyst is returned to reaction zone.

In an alternative embodiment, and particularly where the dehydrocyclization reaction is conducted in a fixed bed reactor, the regeneration can be conducted without removal of the catalyst from the reaction zone, by temporarily discontinuing the supply of methane-containing feedstock to the reaction zone, heating the reaction zone to a regeneration temperature of about 700° C. to about 1200° C. by direct and/or indirect contact with combustion gases produced by combustion of a supplemental fuel, regenerating the particulate catalytic material with a hydrogen-containing gas, and then re-establishing the supply of methane-containing feedstock to the reaction zone. It is to be appreciated that heating the reaction zone to the regeneration temperature can be effected before the supply of methane-containing feedstock is discontinued.

Catalyst Reheating

Since the dehydrocyclization reaction is endothermic, it is necessary to supply heat to the reaction. In the present process, this is conveniently achieved by withdrawing part of the catalyst from the reaction zone, either on an intermittent or a continuous basis, supplying heat to the catalyst and then returning the heated catalyst back to the reaction zone. Since the hydrogen regeneration step described above also involves heating the catalyst and then recycling the heated regenerated catalyst back to the reaction zone, one possible route for supplying heat to the dehydrocyclization reaction is by means of the regeneration process.

Alternatively, some or all of the heat required to maintain the dehydrocyclization reaction can be supplied by a separate catalyst reheating step. In this embodiment, part of the catalyst withdrawn for the reaction zone is transferred to a separate heating zone, where again the catalyst is heated by direct or indirect contact with hot combustion gases generated by burning a supplemental source of fuel. The heated catalyst is then returned to the reaction zone with or without undergoing hydrogen regeneration.

Catalyst Recarburizing

It will be appreciated that heating the dehydrocyclization catalyst for the purposes of regeneration and/or for heat transfer back the dehydrocyclization reaction may subject the catalyst to high temperature oxidizing conditions, especially where catalyst heating involves direct contact with hot combustion gases. As a result, metals, such as rhenium, tungsten or molybdenum, present in the dehydrocyclization catalyst may be converted during the heating step from their catalytically active elemental or carbide form to an oxide species. Thus, before being returned to the reaction zone, the regenerated and/or reheated catalyst may be transferred to a catalyst treatment zone separate from the regeneration zone, the heating zone and the reaction zone, where the catalyst is contacted with a carburizing gas containing at least one hydrocarbon selected from methane, ethane, propane, butane, isobutene, hexane, benzene and naphthalene. In some cases, the carburizing gas may also contain at least one of $CO_2$, CO, $H_2$, $H_2O$ and inert diluents. Alternatively, the carburizing gas may be a mixture of hydrogen and at least one of CO and $CO_2$. Moreover, it may be desirable to contact the catalyst sequentially with a plurality of different carburizing gases, each comprising a hydrocarbon selected from methane, ethane, propane, butane, isobutene, hexane, benzene and naphthalene or a mixture of hydrogen and at least one of CO and $CO_2$.

To avoid damage to the catalyst, the carburization process is controlled so that the maximum temperature in the catalyst treatment zone is less than the maximum temperature in the dehydrocyclization reaction zone, although typically the maximum carburization temperature is higher than the maximum temperature reached in the regeneration zone. Generally the maximum temperature in the catalyst treatment zone is from about 400° C. to about 1100° C., such as from about 500° C. to about 900° C., with the minimum temperature being between 300° C. and 500° C. Typically, the catalyst treatment zone is operated at pressures between 10 and 100 psia (69 and 690 kPa), such as between 15 and 60 psia (103 and 414 kPa). Generally, the average residence time of catalyst particles in the catalyst treatment zone will be between 0.1 and 100 minutes, for example between 1 and 20 minutes. Under these conditions, the carburizing gas reacts with metal oxide species on the catalyst to return the metal to its catalytically active elemental or carbidic form. In addition, the carburizing gas can react with active surface sites on the catalyst support to decrease their tendency to generate coke in the dehydroaromatization reaction zone.

To maintain the temperature required for carburization of the regenerated catalyst, heat can supplied to the catalyst and/or the carburizing gas prior to or during the carburization step. For example heat can be supplied to the catalyst by indirect heating, by contacting with hot flue gas from the reaction zone or the heating zone, by contacting with the hot gaseous effluent from the carburization process, or by mixing with heated catalyst from the heating zone. Heat is conveniently supplied to the carburization gas by means of an external furnace or heat exchanger or by with heated catalyst from the heating zone.

The catalyst treatment zone may be operated as a fluidized bed reactor, ebulating bed reactor, settling bed reactor, riser reactor or circulating riser reactor. In one embodiment, the catalyst treatment zone comprises a settling bed reactor. Alternatively, the catalyst treatment zone comprises a single fluidized bed reactor with internal baffles to prevent backmixing or a plurality of fluidized bed reactors in series with the regenerated catalyst being cascaded between adjacent reactors. In any event, contact in the catalyst treatment zone is facilitated by arranging that the regenerated catalyst and the carburizing gas flow in opposite directions in said catalyst treatment zone. Employing such a countercurrent flow, a temperature profile may be developed in the catalyst treatment zone such that carburization of the regenerated catalyst initially occurs at a low temperature but the carburization temperature increases as the catalyst flows through the bed.

In some cases, it may be desirable that the heated unregenerated catalyst is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

Catalyst Make-Up

In practice, as the dehydrocyclization reaction proceeds, fresh dehydrocyclization catalyst will be added to the process to make up for catalyst lost by mechanical attrition and/or deactivation. Moreover, as the reaction proceeds and the catalyst in the reaction zone is subjected to repeated coking and regeneration sequences, the total amount of Bronsted acid sites in the catalyst inventory is likely to vary form the optimal value. Thus, in one embodiment, the composition and/or rate of addition fresh dehydrocyclization catalyst is controlled such that the ratio of the amount of any Bronsted acid sites in the total catalyst inventory in the reaction to the amount of said metal in the catalyst inventory is less than 0.1 mol/mol of said metal.

Although there are multiple means of addition of fresh catalyst, to avoid damage to the catalyst, it is generally desirable to add fresh catalyst to a region of the process that is operating at a temperature below the maximum temperature in the or each dehydrocyclization reaction zone. In one embodiment, fresh dehydrocyclization catalyst is added to the process by introduction into the catalyst treatment zone, whereby the fresh catalyst is contacted with the carburizing gas prior to transfer to the reaction zone for contact with the methane-containing feed. In another, embodiment the catalyst may be added to the lower temperature regions of a reactor system with an inverse temperature profile.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, such as CO and/or $CO_2$, to produce water and a second effluent stream having a reduced hydrogen content compared with the first (dehydrocyclization) effluent stream. Suitable hydrogen rejection processes are described below and in our copending PCT Application Serial No. PCT/US2005/044042, filed on Dec. 2, 2005.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least portion of the hydrocarbons are conveniently recycled to the dehydrocyclization step. For example, where the hydrocarbons produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \qquad \text{(Reaction 6)}$$

$$2CO_2 + 7H_2 \leftrightarrow C_2H_6 + 4H_2O \qquad \text{(Reaction 7)}$$

The carbon dioxide employed is conveniently part of a natural gas stream and typically the same natural gas stream used as the feed to the dehydrocyclization step. Where the carbon dioxide is part of a methane-containing stream, the $CO_2$:$CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2$:$CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and conveniently greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2:CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, such as about 1.5:1 to about 2.5:1, at a temperature of about 175° C. to about 400° C., such as about 180° C. to about 240° C. and a pressure of about 1 to about 100 bar (100 to 10,000 kPa), such as about 10 to about 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, especially cobalt, with rhenium or zirconium as a promoter, especially cobalt and rhenium supported on silica or titania, generally titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$—ZnO and ZSM-5 Catalysts for the Transformation of Syngas into Liquid Hydrocarbons* by Jose Erena; Ind. Eng. Chem. Res. 1998, 37, 1211-1219, incorporated herein by reference.

The Fischer-Tropsch liquids, i.e., $C_5$+, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \quad \text{(Reaction 8)}$$

and by the following reaction:

$$CH_4 + H_2O \leftrightarrow CO + 3H_2$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from about 0.5:1 to about 20:1, such as in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, for example from about 500 $hr^{-1}$ to about 10,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of: i) at least one metal from Group 3 and at least one metal from Groups 4-15 of the Periodic Table of the Elements; ii) at least one metal from Groups 5-15 of the Periodic Table of the Elements, and at least one metal from at least one of Groups 1, 2, and 4 of the Periodic Table of the Elements; iii) at least one metal from Groups 1-2, at least one metal from Group 3, and at least one metal from Groups 4-15 of the Periodic Table of the Elements; and iv) two or more metals from Groups 4-15 of the Periodic Table of the Elements; and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

In addition to hydrogen, the other major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). Suitable alkylation and hydrogenation processes are described below and in more detail in our copending PCT Application Serial Nos. PCT/US2005/043523, filed on Dec. 2, 2005 and PCT/US2005/044038, filed on Dec. 2, 2005.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e, those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 $hr^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 $hr^{-1}$ and a mole ratio of benzene to ethylene of from 1:1 to 30:1.

Conveniently, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 $sec^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 $hr^{-1}$ to about 50,000 $hr^{-1}$, such as about 250 $hr^{-1}$ to about 25,000 $hr^{-1}$, more for example about 500 $hr^{-1}$ to about 10,000 $hr^{-1}$.

The effluent from the reverse shift reactor can then be fed to an alkylation reactor operating under conditions to cause reactions such as the following to occur:

$$CO+2H_2 \leftrightarrow CH_3OH \quad \text{(Reaction 9)}$$

$$CH_3OH+C_6H_6 \rightarrow toluene+H_2O \quad \text{(Reaction 10)}$$

$$2CH_3OH+C_6H_6 \rightarrow xylenes+2H_2O \quad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 $hr^{-1}$. A suitable catalyst would comprise a molecular sieve having a constraint index of 1 to 12, such as ZSM-5, typically together with one or metals or metal oxides, such as copper, chromium and/or zinc oxide.

Conveniently, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, such as a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

The invention will now be more particularly described with reference to the accompanying drawings and the following non-limiting Examples.

In the Examples, measurements of the amount of Bronsted acid sites in a catalyst are made using an NMR procedure for determining the proton density of the catalyst. In particular, the catalyst proton density is determined using a shallow bed CAVERN device, as shown in FIG. 1. Thus, referring to FIG. 1, the CAVERN device comprises an upper housing 5 and lower housing 6 connected by a joint 12. The device also includes a mechanism 11 for lifting a glass trapdoor 16 from a catalyst bed 14, a line 20 for connecting the housing 5, 6 to a vacuum pump, and thermocouple 13 for heating a catalyst sample in the bed 14. A 5 mm outside diameter glass tube 17 slides over a 3 mm diameter stainless steel rod 15, and rests between an endcap 18 and the glass trapdoor 16. The stainless steel rod 15 is retracted by turning the mechanism 11, whereby the glass tube 17 raises the glass trapdoor 16 above the catalyst bed 14. By gently turning or shaking the CAVERN device, the catalyst sample (not shown) falls into a Magic Angle Spinning (MAS) rotor 19.

In order to determine the proton density of a catalyst sample, a thin layer of the sample is spread out in the catalyst bed 14 and then any moisture absorbed on the catalyst sample is removed by evacuating the housing 5, 6 and raising the temperature of the catalyst sample to 350° C. via thermocouple 13. The catalyst sample is typically held under vacuum (such as $1\times10^{-5}$ kPa) at 350° C. for 3 hours prior to NMR measurement. The dried catalyst sample is then loaded into a 5 mm NMR rotor, such as MAS rotor 19, and the rotor is sealed with a Kel-F end cap by manipulating the CAVERN device. All the operations are performed while the catalyst sample is still under vacuum, ensuring the sample integrity for NMR study.

$^1$H NMR experiments are performed on a 400 MHz solid state NMR spectrometer operating at 399.8 MHz for 1H. The NMR spectrometer used is a Varian Infinity Plus 400 MHz solid state NMR with an Oxford AS400 magnet. Quantitative $^1$H spectra are obtained by the use of rotor-synchronized spin-echo sequence ($\pi/2$-$t_{D1}$-$\pi$-$t_{D2}$-Echo) using 8 to 12 kHz spinning speeds. Typically, 3.5-μs $\pi/2$ pulses, $t_{D1}$ of 125-μs and $t_{D2}$ of 113.1 μs are used for a spinning speed of 9 kHz. Spectra acquired using the solid echo sequence show some background signal, presumably from the spinning module and the endcap 18 of the MAS rotor 19. A solid echo sequence with DEPTH removes the background signal from the spectra. The DEPTH sequence consists of a 900 pulse (3.5-μs) followed by two 180° pulses. A description of the DEPTH sequence appears in Corey, D. G.; Ritchey, W. M. *J. Magn. Reson.* 1988, 80, 128, incorporated herein by reference. A pulse delay of 10 seconds is sufficient for quantifying proton density of the catalyst samples tested. Acetone is used as secondary standard for $^1$H shift (2.1 ppm). All the reported chemical shifts are referenced to tetramethylsilane (TMS) at 0 ppm.

After the desired NMR spectra have been acquired, the weight of MAS rotor 19, the catalyst sample and the endcap 18 are determined followed by weight determination of the rotor and the endcap 18 upon unpacking the catalyst sample. The difference in the two weights is the amount of the catalyst sample in the MAS rotor 19.

Further details regarding the operation of the CAVERN device are disclosed in Xu, T.; Haw, J. F. *Top. Catal.* 1997, 4, 109-118, incorporated herein by reference.

EXAMPLE 1

Example 1 demonstrates the effect of hydrogen pre-treatment at 850° C. on the coking rate of HZSM-5 in methane aromatization.

As a comparison, a thermogravimetric (TGA) experiment was conducted in which a HZSM-5 sample (silica/alumina molar ratio of about 13) was initially heated to 500° C. and kept at 500° C. in He for 1 hr to remove any adsorbed water. The temperature was then ramped to 800° C. under methane flow (40 ml/min) and kept in methane at 800° C. for 80 mins.

Figure 2A:
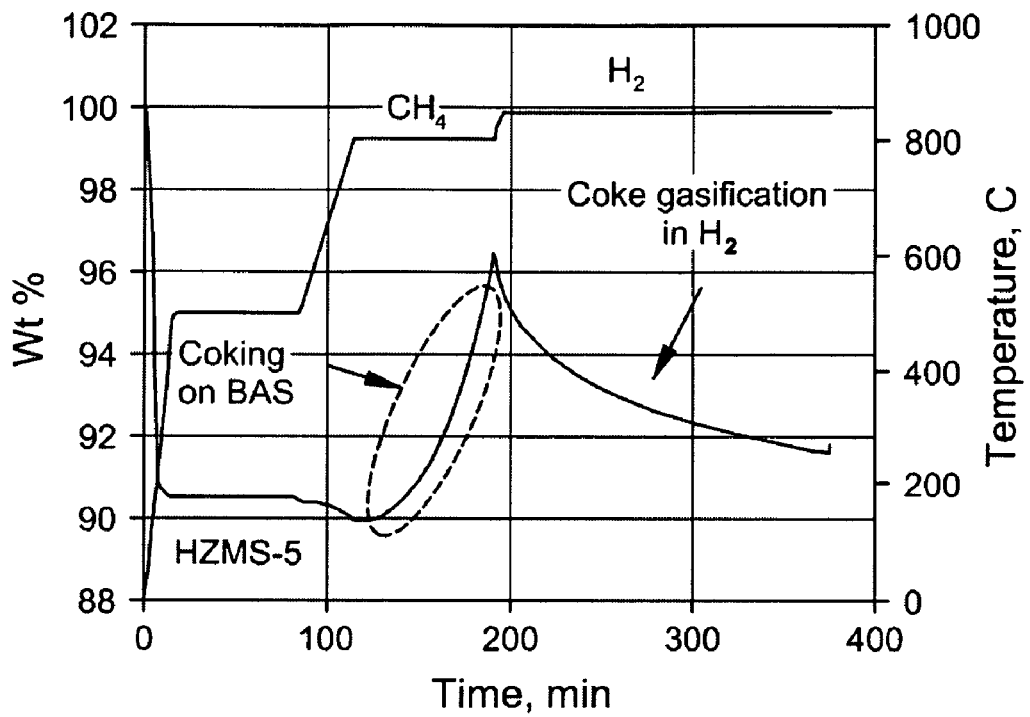
[FIG. 2(*b*)].
Figure 2B:
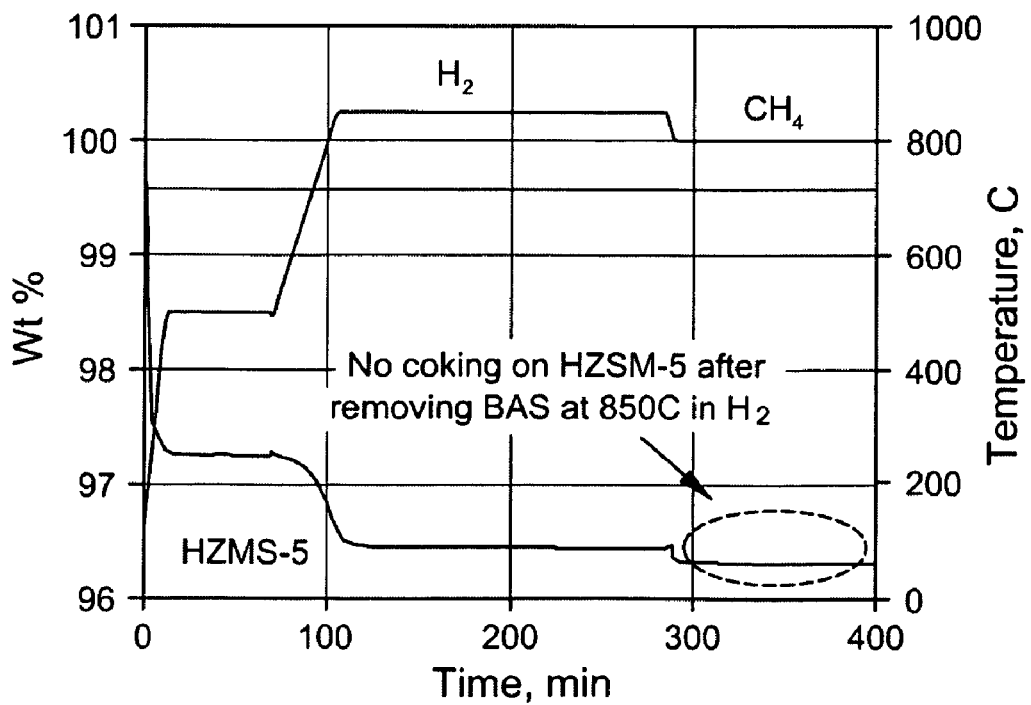

The results are shown in FIG. 2 (a), in which the upper line represents temperature and the lower line indicates % weight change. It will be seen that the sample exhibited a significant increase in weight at 800° C. (7 wt % increase) while under methane flow due to the coke accumulation on Bronsted acid sites. This was verified by treating the catalyst after methane flow with $H_2$ at 850° C. It will be seen that the $H_2$ treatment at 850° C. resulted in a significant weight loss caused by coke gasification. Separate $^1$H NMR experiments indicated that the fresh catalyst contained about 1 mmol/g of Bronsted acid sites.

FIG. 2 (b) shows the results of a similar TGA experiment to that shown in FIG. 2 (a), except that, prior to the introduction of methane at 800° C., the HZSM-5 was heated at 850° C. in $H_2$ for 200 minutes to reduce the number of zeolite Bronsted acid sites via dealumination. The subsequent exposure to methane following the $H_2$ treatment did not lead to any weight increase, suggesting that coke formation on the catalyst was completely eliminated.

EXAMPLE 2

A Mo/ZSM-5 catalyst containing 5 wt % Mo was prepared from HZSM-5 having a silica/alumina molar ratio of about 13 by wet impregnation using the following procedure. 0.91 gm of ammonium heptamolybdate hydrate (AHM) purchased from Aldrich was dissolved in 10.5 g of water and was mixed with 10 g of HZSM-5 under constant stirring for 0.5 hour. The mixture was then calcined in air following the temperature program—ramp from room temperature at 5° C./min to 70° C., hold for 2 hours, ramp from 70° C. at 5° C./min to 120° C., hold for 2 hours, ramp from 120° C. at 5° C./min to 500° C., and hold 500° C. for 6 hours—to give a catalyst having a nominal Mo loading of 5 wt %.

Figure 3A:
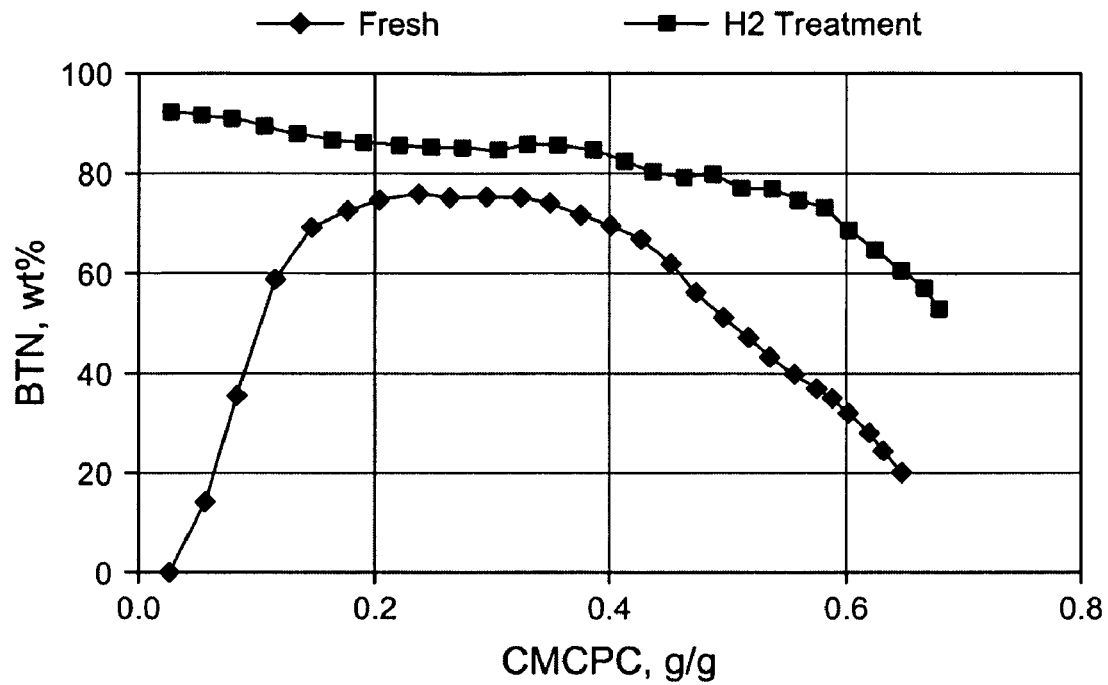
FIG. 3(*a*) is a graph plotting selectivity to benzene, toluene and naphthalene against Cumulative Methane Converted Per Gram of Catalyst (CMCPC) and FIG. 3(*b*) is a graph plotting conversion against CMCPC for the fresh 5 wt % Mo/ZSM-5 of Example 2 and for the coked 5 wt % Mo/ZSM-5 of Example 2 after hydrogen treatment at 850° C. for 60 hours.
Figure 3B:
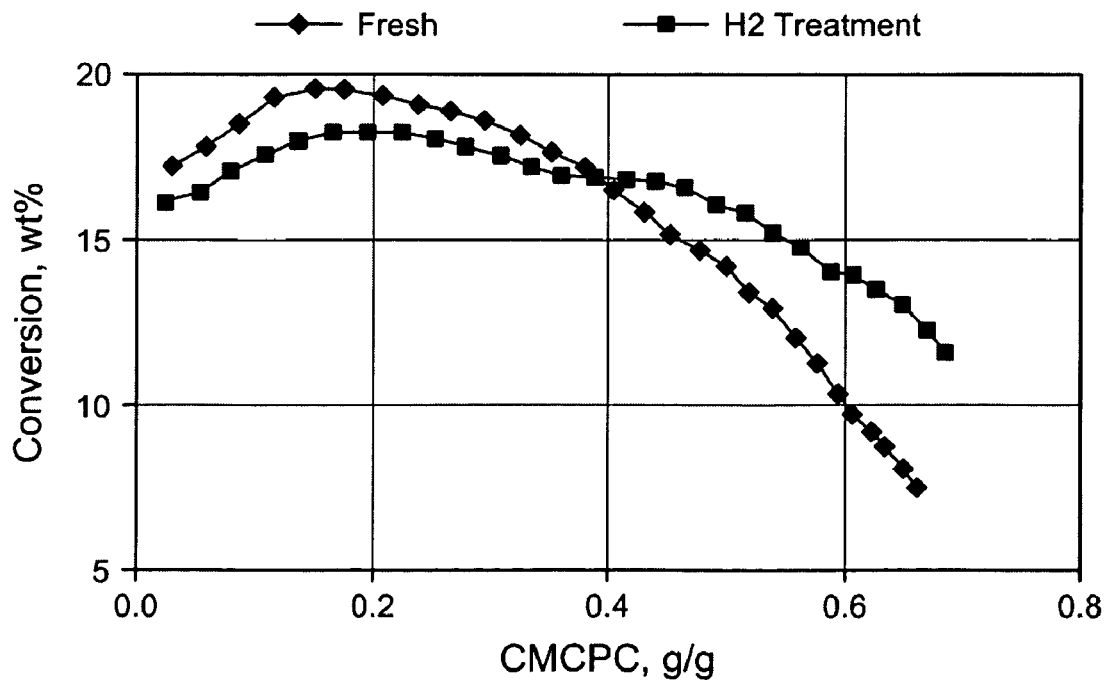

The resultant catalyst was then used to convert methane to aromatic hydrocarbons at 800° C., 14 psia (97 kPaa) and 1.2 WHSV and the results are shown by the diamond points in FIGS. 3 (a) and (b). After methane conversion decreased to around 7%, the supply of methane was stopped and the sample was treated at 850° C. in $H_2$ for about 60 hrs to remove coke accumulated on the catalyst. After the treatment, the performance of the sample was evaluated using the same methane conversion conditions as those of the fresh sample. The square points in FIGS. 3 (a) and (b) show selectivity and conversion rate of the treated catalyst and demonstrate that the selectivity of the treated sample, presumably after removing acid sites, showed significant improvement over the fresh sample. Moreover, although the initial conversion of methane was slightly lower after the removal of acid sites, the treated catalyst showed longer lifetime.

EXAMPLE 3

A Mo/ZSM-5 catalyst containing 2.7 wt % Mo was prepared from HZSM-5 having a silica/alumina molar ratio of about 13 by the same wet impregnation procedure as used in Example 2.

Figure 4:
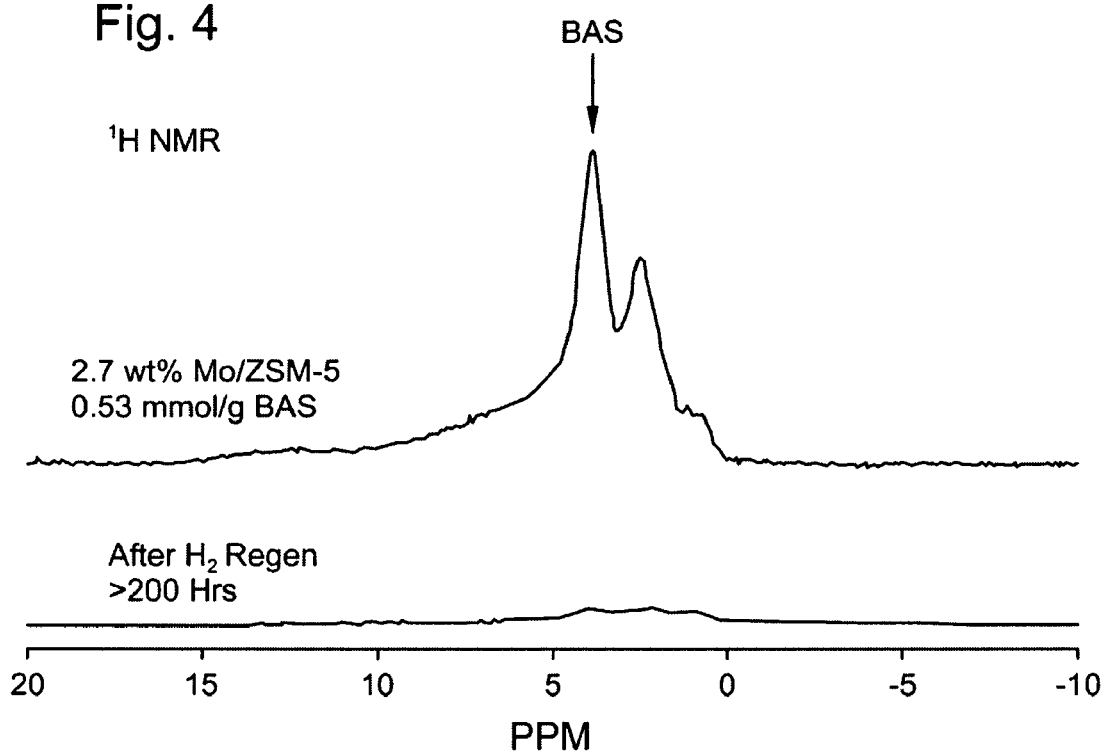
FIG. 4 shows the $^1$H NMR spectra of the 2.7 wt % Mo/ZSM-5 catalyst of Example 3 when fresh and after repeated and alternating methane conversion and hydrogen regeneration steps.

The resultant catalyst was subjected to $^1$H NMR (see upper line in FIG. 4), which demonstrated the presence of 0.53 mmol of Bronsted acid sites per gram of the fresh catalyst.

Figure 5:
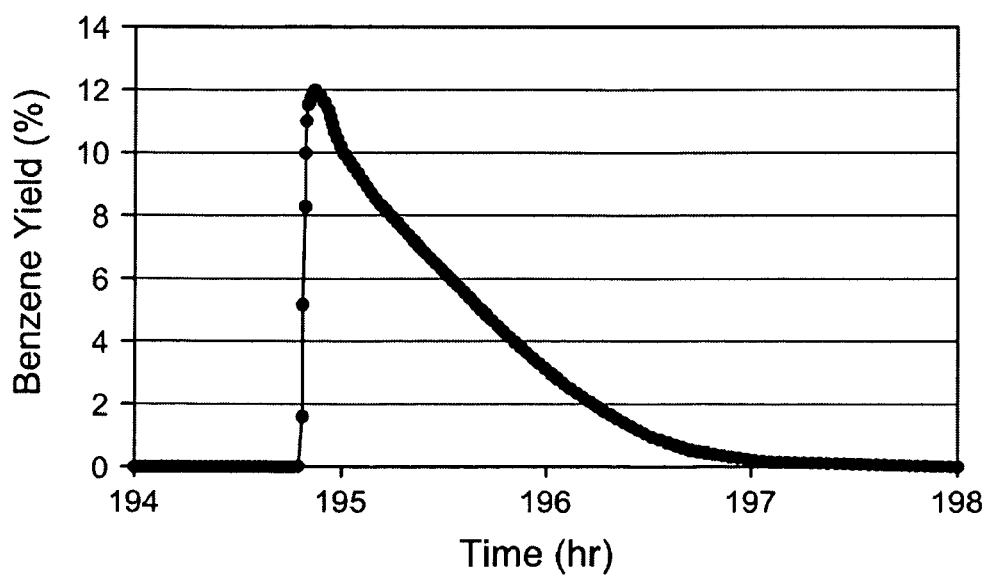
FIG. 5 is a graph plotting benzene yield against time during the process of repeated and alternating methane conversion and hydrogen regeneration steps of Example 3.

The catalyst was then used to convert methane to aromatic hydrocarbons in a process in which the catalyst was subjected to multiple and alternating methane conversion and hydrogen regeneration cycles. In each methane conversion cycle, the catalyst was contacted with a mixture of 95% methane, 5% argon at 800° C. and 15 psia (103 kPaa). The weight hourly space velocity (WHSV) for each methane conversion cycle was varied and ranged from 0.3 to 1.2 hr$^{-1}$. In each hydrogen regeneration cycle, the catalyst was contacted with 15 psia (103 kPaa) hydrogen at a temperature which ranged from 800 to 900° C. The WHSV for each hydrogen regeneration cycle was varied and ranged from 0.15 to 1.0 hr$^{-1}$. The catalyst was run for 200 hours with a total of 25 methane conversion cycles alternating with 25 hydrogen regeneration cycles. The ratio of the time spent on methane conversion to the time spent on hydrogen regeneration was 0.26. After a total of 200 hours on stream and after a hydrogen regeneration cycle, the catalyst was subjected to air oxidation at 550° C. for 5 hours to remove any residual coke and the $^1$H NMR spectrum of the catalyst was again run. The results are shown by the lower line in FIG. 4 and demonstrated the substantial absence of Bronsted acid sites (<0.04 mmol/g). However, the reactor data acquired prior to the end of the multi-cycle treatment showed good performance as shown in FIG. 5, which shows the benzene yield during the final methane conversion cycle at 800° C., 15 psia (103 kPaa), 1.2 hr$^{-1}$ WHSV.

EXAMPLE 4

An HZSM-5 sample having a silica/alumina molar ratio of about 13 was subjected to $^1$H NMR which, as shown in FIG. 6(a) demonstrated the presence of 1 mmol of Bronsted acid sites and 0.3 mmol of silanol sites per gram of the zeolite.

The HZSM-5 sample was then used to produce a Mo/ZSM-5 catalyst containing 1.8 wt % Mo by the same wet impregnation procedure as used in Example 2. The resultant catalyst was subjected to $^1$H NMR which, as shown in FIG. 6(b) demonstrated the presence of 0.59 mmol of Bronsted acid sites and 0.29 mmol of silanol sites per gram of the fresh catalyst.

The catalyst sample was then exposed to 15 wt % methane/85 wt % hydrogen at 800° C. for 1 hr followed by 100% methane for 1 hr at 800° C. and, as shown in FIG. 6(c), $^1$H NMR demonstrated that the acid density and silanol density had decreased to 0.31 and 0.16 mmol/g, respectively. Subsequent exposure of the sample to $H_2$ at 850° C. led to an acid density of 0.21 mmol/g, a further 30% reduction in acid density, see FIG. 6(d).

EXAMPLE 5

A quartz reactor was loaded with 0.7 g of a ZSM-5 catalyst with a silica/alumina molar ratio of about 13 and a nominal 4 wt % Mo. This catalyst was run with alternating methane aromatization and hydrogen regeneration cycles, at 7 psig (149 kPa). The feed during each methane aromatization cycle was composed of Ar 10%, $CH_4$ 86.65%, $C_2H_6$ 1.8%, $CO_2$ 0.9%, and $H_2$ 0.45% by volume and was supplied at 22.2 standard cc/minute. During each 20 minute methane aromatization cycle, the temperature of the reactor was held at about 700° C. for 9 minutes, then ramped to 800° C. at 20° C./minute, then held at 800° C. for the last 6 minutes, and finally the effluent gas composition was measured by gas chromatograph. Conversion of the feed hydrocarbons, and selectivities to various products, were calculated from the feed and effluent compositions. The hydrogen regeneration phase of each cycle lasted a total of 40 minutes, with $H_2$ flow of 50 sccm. During this 40 minutes, the temperature was ramped from 800 to 850° C. at 20° C./min, held for 30 minutes at 850° C., and cooled to 700° C. in about 7.5 minutes. Thus, during each 60 minute aromatization/regeneration cycle, the catalyst spent ⅔ of the time under high temperature hydrogen.

The results are shown in Table 1, from which it will be seen that, with the described treatment, the catalyst selectivity to benzene and toluene increased, while selectivity to coke and naphthalene decreased, as the reaction proceeded.

TABLE 1

|  | Time on Stream, hr | | | |
| --- | --- | --- | --- | --- |
|  | 2.55 | 4.58 | 7.63 | 76.77 |
| ($CH_4$ + $C_2H_6$) Conversion | 22.27 | 21.95 | 21.65 | 19.80 |
| Benzene Yield, % carbon | 10.46 | 11.63 | 12.59 | 13.30 |
| Carbon Selectivity from converted $CH_4$ + $C_2H_6$ | | | | |
| Benzene | 46.96 | 52.98 | 58.16 | 67.18 |
| Toluene | 1.91 | 2.20 | 2.48 | 3.39 |
| Naphthalene | 26.23 | 22.93 | 18.78 | 11.83 |
| Coke | 16.55 | 13.47 | 12.33 | 8.47 |

The NMR results together with the reactor performance data suggest that Bronsted acid sites are not needed for methane conversion. In fact, it is advantageous to remove the Bronsted acidity prior to methane conversion to improve selectivity for aromatics and to reduce coke selectivity. These conclusions about the role of Bronsted acid sites in methane aromatization are in direct contrast with the literature teachings discussed above.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for converting a low carbon number aliphatic hydrocarbon to higher hydrocarbons including aromatic hydrocarbons, the process comprising contacting a feed containing said aliphatic hydrocarbon with a dehydrocyclization catalyst under conditions effective to convert said aliphatic hydrocarbon to aromatic hydrocarbons and produce an effluent stream comprising aromatic hydrocarbons and hydrogen, wherein said dehydrocyclization catalyst comprises at least one metal, said metal selected from at least one of molybdenum, rhenium, and tungsten, and a molecular sieve comprising ZSM-5 and wherein the ratio of the amount of any Bronsted acid sites in the molecular sieve to the amount of said at least one metal is less than 0.1 mol/mol of said at least one metal, including a step, prior to said contacting step, of pretreating said catalyst to reduce the number of said Bronsted acid sites in said molecular sieve, wherein said pretreatment to reduce the number of said Bronsted acid sites comprises heating said catalyst in the presence of a gas comprising hydrogen and optionally at least one low carbon number aliphatic hydrocarbon.

2. The process according to claim 1, wherein the molar ratio of Bronsted acid sites in said molecular sieve to said at least one metal is less than 0.01.

3. The process according to claim 1, wherein the molar ratio of Bronsted acid sites in said molecular sieve to framework Al in said molecular sieve is less than 0.1.

4. The process according to claim 1, wherein said pretreatment to reduce the number of said Bronsted acid sites reduces the number of Bronsted acid sites by at least 50%.

5. The process according to claim 1, wherein the molecular sieve is an aluminosilicate having an as-synthesized silica to alumina molar ratio of less than 100.

6. The process according to claim 1, wherein the feed comprises methane.

7. The process according to claim 1, further characterized by:
(a) contacting a feed containing said aliphatic hydrocarbon with said dehydrocyclization catalyst in a reaction zone under conditions effective to convert said aliphatic hydrocarbon to aromatic hydrocarbons and generate coke on said catalyst;
(b) periodically contacting a portion of said catalyst with a regeneration gas comprising hydrogen under conditions effective to at least partially remove coke from said portion of said catalyst;
(c) adding fresh dehydrocyclization catalyst to make up for losses of said catalyst during (a) and (b), wherein said addition is controlled such that the molar ratio of the amount of any Bronsted acid sites in said molecular sieve to the amount of said at least one metal is maintained at less than 0.1.

8. The process according to claim 1, including a step of alkylating a portion of the aromatic product to produce a composition comprising p-xylene.

9. The process according to claim 7, wherein, in step (c), the molar ratio of the amount of any Bronsted acid sites in said molecular sieve to the amount of said at least one metal is maintained at less than 0.01.

* * * * *